United States Patent
Roszell

(10) Patent No.: US 8,299,122 B2
(45) Date of Patent: Oct. 30, 2012

(54) METHOD FOR STABILIZING RETINOIC ACID, RETINOIC ACID CONTAINING COMPOSITION, AND METHOD OF USING A RETINOIC ACID CONTAINING COMPOSITION

(75) Inventor: James A. Roszell, Henderson, NV (US)

(73) Assignee: Skinvisible Pharmaceuticals, Inc., Las Vegas, NV (US)

( * ) Notice: Subject to any disclaimer, the term of this patent is extended or adjusted under 35 U.S.C. 154(b) by 0 days.

(21) Appl. No.: 12/423,616

(22) Filed: Apr. 14, 2009

(65) Prior Publication Data

US 2009/0264527 A1    Oct. 22, 2009

Related U.S. Application Data

(60) Provisional application No. 61/124,212, filed on Apr. 14, 2008.

(51) Int. Cl.
*A61K 31/04* (2006.01)

(52) U.S. Cl. ........ 514/559; 514/558; 514/557; 514/553; 554/221; 554/175; 554/2

(58) Field of Classification Search .......... None
See application file for complete search history.

(56) References Cited

U.S. PATENT DOCUMENTS

| | | | |
|---|---|---|---|
| 3,729,568 A | 4/1973 | Kligman | |
| 3,817,887 A | 6/1974 | Mestetsky | |
| 3,957,966 A * | 5/1976 | Valan | 424/482 |
| 4,035,506 A | 7/1977 | Lucas et al. | |
| 4,126,699 A | 11/1978 | Gander et al. | |
| 4,139,625 A | 2/1979 | Sherlock | |
| 4,189,501 A | 2/1980 | Fulton, Jr. | |
| 4,301,145 A | 11/1981 | Cestari | |
| 4,384,903 A | 5/1983 | Enever | |
| 4,440,741 A | 4/1984 | Marschner | |
| 4,448,906 A | 5/1984 | Deinet et al. | |
| 4,500,338 A | 2/1985 | Young et al. | |
| 4,507,279 A | 3/1985 | Okuyama et al. | |
| 4,645,794 A | 2/1987 | Davis et al. | |
| 4,671,957 A | 6/1987 | Holtshousen | |
| 4,677,120 A | 6/1987 | Parish et al. | |
| 4,803,066 A | 2/1989 | Edwards | |
| 4,810,489 A | 3/1989 | Murray et al. | |
| 4,840,687 A | 6/1989 | Forsberg et al. | |
| 4,885,311 A | 12/1989 | Parish et al. | |
| 4,897,259 A | 1/1990 | Murray et al. | |
| 4,971,800 A | 11/1990 | Chess et al. | |
| 5,019,604 A | 5/1991 | Lemole | |
| 5,045,317 A | 9/1991 | Chess et al. | |
| 5,049,584 A | 9/1991 | Purcell et al. | |
| 5,051,260 A | 9/1991 | Chess et al. | |
| 5,055,303 A | 10/1991 | Riley, Jr. | |
| 5,082,656 A | 1/1992 | Hui et al. | |
| 5,124,356 A | 6/1992 | Purcell et al. | |
| 5,126,136 A | 6/1992 | Merat et al. | |
| RE34,075 E | 9/1992 | Purcell et al. | |
| 5,155,199 A | 10/1992 | Hayashi | |
| 5,232,691 A | 8/1993 | Lemole | |
| 5,266,329 A | 11/1993 | Riley, Jr. | |
| 5,298,534 A | 3/1994 | Prosise et al. | |
| 5,312,834 A | 5/1994 | Yeo | |
| 5,320,838 A | 6/1994 | Woller | |
| 5,336,305 A | 8/1994 | Staats | |
| 5,370,876 A | 12/1994 | Noll et al. | |
| 5,389,363 A | 2/1995 | Snyder et al. | |
| 5,417,968 A | 5/1995 | Staats | |
| 5,431,756 A | 7/1995 | Kosowski et al. | |
| 5,460,620 A * | 10/1995 | Smith et al. | 604/290 |
| 5,508,024 A | 4/1996 | Tranner | |
| 5,597,849 A | 1/1997 | McGinity et al. | |
| 5,605,676 A | 2/1997 | Gaffar et al. | |
| 5,607,979 A | 3/1997 | McCreery | |
| 5,622,993 A | 4/1997 | McGinity et al. | |
| 5,658,559 A | 8/1997 | Smith | |
| 5,707,612 A | 1/1998 | Zofchak et al. | |
| 5,721,306 A | 2/1998 | Tsipursky et al. | |
| 5,725,844 A | 3/1998 | Gers-Barlag et al. | |
| 5,725,875 A | 3/1998 | Noll et al. | |
| 5,730,966 A | 3/1998 | Torgerson et al. | |
| 5,736,128 A | 4/1998 | Chaudhuri et al. | |
| 5,747,022 A | 5/1998 | Slavtcheff | |

(Continued)

FOREIGN PATENT DOCUMENTS

DE      195 43 989 A1      5/1997

(Continued)

OTHER PUBLICATIONS

"Altered chemical and biological activities of all-trans retinoic acid incorporated in solid lipid nanoparticle powders" by Lim et al., J. Controlled Release 100, 53-61 (2004).*
U.S. Appl. No. 12/445,827, filed Apr. 16, 2009, Roszell, James A.
Bradley, C. et al., "Noninvasive Transdermal Chemical Collection", *Skin Pharmacol*, pp. 218-226 (1990).
Hasirci V., "Synthesis and characterization of PVNO and PVNO-PVP hydrogels", *Biomaterials*, vol. 2, No. 1, 7 pages (Jan. 1981).
Material Safety Data Sheet, Gantrez S-97 BF Solution, ISP Technologies, Inc., 6 pages (Apr. 7, 1994).
Material Safety Data Sheet, Ganez V-216, ISP Technologies, Inc., pp. 5 pages (Sep. 16, 1994).

(Continued)

*Primary Examiner* — Brandon Fetterolf
*Assistant Examiner* — Theodore R West
(74) *Attorney, Agent, or Firm* — Merchant & Gould, P.C.

(57) ABSTRACT

A method for stabilizing retinoic acid is provided. The method includes a step of mixing retinoic acid with a hydrophobic polymer/hydrophilic polymer adduct in the presence of an oxygen containing atmosphere to form a retinoic acid containing composition. The hydrophobic polymer/hydrophilic polymer adduct comprises a poly(vinylpyrrolidone/alkylene) polymer and a polymer comprising repeating carboxylic acid groups, hydroxyl groups, or a mixture of carboxylic acid groups and hydroxyl groups. A retinoic acid containing composition and a method of using a retinoic acid containing composition are provided.

24 Claims, No Drawings

U.S. PATENT DOCUMENTS

| | | | |
|---|---|---|---|
| 5,807,957 | A | 9/1998 | Samour et al. |
| 5,834,538 | A | 11/1998 | deHullu et al. |
| 5,874,074 | A | 2/1999 | Smith |
| 5,891,470 | A | 4/1999 | Rinaldi et al. |
| 5,906,822 | A | 5/1999 | Samour et al. |
| 5,911,980 | A | 6/1999 | Samour et al. |
| 5,939,453 | A | 8/1999 | Heller et al. |
| 5,942,545 | A | 8/1999 | Samour et al. |
| 5,955,109 | A | 9/1999 | Won et al. |
| 5,968,543 | A | 10/1999 | Heller et al. |
| 5,968,919 | A | 10/1999 | Samour et al. |
| 5,976,566 | A | 11/1999 | Samour et al. |
| 5,980,876 | A | 11/1999 | Peffly |
| 6,096,344 | A | 8/2000 | Liu et al. |
| 6,117,843 | A | 9/2000 | Baroody et al. |
| 6,150,403 | A | 11/2000 | Biedermann et al. |
| 6,159,493 | A | 12/2000 | Chen et al. |
| 6,168,798 | B1 | 1/2001 | O'Halloran et al. |
| 6,177,068 | B1 | 1/2001 | Shih et al. |
| 6,183,766 | B1 | 2/2001 | Sine et al. |
| 6,190,689 | B1 | 2/2001 | Hoffmann et al. |
| 6,255,421 | B1 | 7/2001 | Plochocka et al. |
| 6,433,024 | B1 | 8/2002 | Popp et al. |
| 6,582,683 | B2 | 6/2003 | Jezior |
| 6,583,220 | B1 | 6/2003 | Lipman |
| 6,627,217 | B1 | 9/2003 | Suzuki et al. |
| 6,756,059 | B2 | 6/2004 | Roszell et al. |
| 6,881,400 | B2 | 4/2005 | Collin |
| 7,008,647 | B2 | 3/2006 | Burrell et al. |
| 2003/0044374 | A1 | 3/2003 | Roszell et al. |
| 2005/0089491 | A1 | 4/2005 | Collin |
| 2005/0118214 | A1 | 6/2005 | Najdek et al. |
| 2005/0175571 | A1 | 8/2005 | Roszell et al. |
| 2005/0276853 | A1* | 12/2005 | Baichwal et al. ............. 424/469 |
| 2005/0287097 | A1* | 12/2005 | Roszell et al. ............. 424/70.13 |

FOREIGN PATENT DOCUMENTS

| | | |
|---|---|---|
| EP | 0260030 A2 | 3/1988 |
| EP | 640352 | 3/1995 |
| EP | 747062 | 12/1996 |
| EP | 391741 | 4/1998 |
| EP | 0 945 120 A | 9/1999 |
| JP | 7089826 | 4/1995 |
| JP | 10095714 A | 9/1996 |
| JP | 10067618 | 3/1998 |
| JP | 2002104920 | 4/2002 |
| WO | WO 93/24105 A | 12/1993 |
| WO | WO 94/23693 A | 10/1994 |
| WO | WO 01/17488 A | 3/2001 |
| WO | WO 03/015821 A1 | 2/2003 |
| WO | WO 2008/051461 A2 | 5/2008 |

OTHER PUBLICATIONS

Material Safety Data Sheet, Ganex V-220, ISP Technologies, Inc., 5 pages (Oct. 7, 1998).

Nair, P. et al., "Studies on the effect of degree of hydrophilicity on tissue response of polyurethane interpenetrating polymer networks", *Biomaterials*, vol. 13, No. 8, pp. 536-542 (1992).

Shinichi, N. et al., "Hair treatment agent—includes specific high molecular copolymer compounds by which skin layer is made to form on hair surface", *Derwent Abstract* (ACC#1998-280363; Week# 199825) (1999).

Tiller et al., "Designing surfaces that kill bacteria on contact", http://www/pnas.org/cgi/content/abstract/98/11/5981, PNAS Online, 2 pages (May 22, 2001).

Declaration of James A. Roszell (with attachments), (April 2, 2009).

Japanese Office Action dated Feb. 7, 2008 from corresponding Japanese patent Application No. 2003-520779.

Canadian Office Action dated Aug. 12, 2009 from corresponding Canadian Application No. 2,457,124.

Australian Office Action dated Aug. 11, 2006 from corresponding Australian Application No. 2002355964.

International Search Report dated Dec. 6, 2002 for corresponding PCT Application No. PCT/US02/26301.

Written Opinion dated Jan. 9, 2004 for corresponding PCT Application No. PCT/US02/26301.

Goddard, E. Desmond; Gruber, James V.; Principles of Polymer Science and Technology in Cosmetics and Personal Care, 1999; Marcel Dekker Inc; (see Entry for PVP/Eicosene copolymer & PVP/Hexadecane), pp. 3,4.

Product Literature for Ganex V-220™, Ganex V-216™ and Ganex WP 660 (download from http.//online1.ispcorp.com on Sep. 29, 2009.

International Search Report from International Application No. PCT/US2007/022299 dated Apr. 21, 2008.

Supplementary European Search Report dated Nov. 5, 2009 and cited references.

* cited by examiner

METHOD FOR STABILIZING RETINOIC ACID, RETINOIC ACID CONTAINING COMPOSITION, AND METHOD OF USING A RETINOIC ACID CONTAINING COMPOSITION

This application claims priority, to the extent appropriate, to U.S. Provisional Patent Application No. 61/124,212 that was filed with the United States Patent and Trademark Office on Apr. 14, 2008. The entire disclosure of U.S. Provisional Patent Application No. 61/124,212 is incorporated herein in its entirety.

FIELD OF THE INVENTION

The invention relates to a method for stabilizing retinoic acid, to a retinoic acid containing composition, and to a method for using a retinoic acid containing composition. Retinoic acid has a tendency to degrade in the presence of visible light and oxygen. By stabilizing retinoic acid, the life and efficacy of compositions containing retinoic acid can be enhanced. The invention additionally relates to a method for stabilizing a retinoid, and to a retinoid containing composition.

BACKGROUND

Retinoids are a class of compounds related to Vitamin A. Retinoids serve many functions in the body such as, cell turnover, growth and renewal, epithelial cell differentiation, vision, bone growth, and collagen formation. Medicinally, retinoids are commonly used in drug applications to treat acne, psoriasis, and skin cancer. More recently, retinol has been used cosmetically in skin anti-aging products mostly because of cell turnover and renewal properties.

Although retinoids are attractive for drug and cosmetic applications, they suffer from a serious drawback. They are unstable to normal room light and oxygen. A variety of techniques for stabilizing retinoids have been tried. In one type of approach, the terminal —OH group of retinol is esterified with various acids from acetic acid to palmitic acid. Although stability of the esterified product is generally better than the parent compound, the biological efficacy is typically decreased. BASF markets a stabilized retinol preparation of a 50% retinol mixture containing vitamins C and E, and the antioxidants butylatedhydroxytoluene and butylatedhydroxyanisole under the name RETISTAR.

The production of products containing retinoids is typically carried out under yellow light and a blanket of inert gas, most often nitrogen or argon, to preserve the retinoid. This considerably increases the cost of production of retinoid containing products. When the customer or patient opens the jar or tube of a product containing a retinoid, decomposition of the retinoid begins as a result of exposure to oxygen and light, and the drug or cosmetic is rendered ineffective in a matter of weeks or a few months at best.

SUMMARY

A method for stabilizing retinoic acid is provided according to the present invention. The method includes a step of mixing a retinoic acid with a hydrophobic polymer/hydrophilic polymer adduct in the presence of an oxygen containing atmosphere to form a retinoic acid containing composition. The hydrophobic polymer/hydrophilic polymer adduct comprises a poly(vinylpyrrolidone/alkylene) polymer and a polymer comprising repeating carboxylic acid groups, hydroxyl groups, or a mixture of carboxylic acid groups and hydroxyl groups.

A retinoic acid containing composition is providing according to the present invention. The retinoic acid containing composition comprises at least about 0.0001 wt. % retinoic acid, at least about 3 wt. % of a hydrophobic polymer/hydrophilic polymer adduct comprising a poly(vinylpyrrolidone/alkylene) polymer and a polymer comprising repeating carboxylic acid groups, hydroxyl groups, or a mixture of carboxylic acid groups and hydroxyl groups, and at least about 50 wt. % water.

A method of using a retinoic acid retinoid containing composition is provided according to the invention. The method includes a step of applying a retinoic acid containing composition to skin tissue.

A method for stabilizing retinoids is provided according to the present invention. The method includes a step of mixing a retinoid with a hydrophobic polymer/hydrophilic polymer adduct in the presence of an oxygen containing atmosphere to form a retinoid containing composition. The hydrophobic polymer/hydrophilic polymer adduct comprises a poly(vinylpyrrolidone/alkylene) polymer and a polymer comprising repeating carboxylic acid groups, hydroxyl groups, or a mixture of carboxylic acid groups and hydroxyl groups.

A retinoid containing composition is providing according to the present invention. The retinoid containing composition comprises about 0.0001 wt. % to about 5 wt. % retinoid, at least about 3 wt. % of a hydrophobic polymer/hydrophilic polymer adduct comprising a poly(vinylpyrrolidone/alkylene) polymer and a polymer comprising repeating carboxylic acid groups, hydroxyl groups, or a mixture of carboxylic acid groups and hydroxyl groups, and at least about 50 wt. % water.

DETAILED DESCRIPTION

A retinoid containing composition is provided that exhibits prolonged retinoid stability even after exposure of the composition to visible light and oxygen. In general, the retinoid containing composition can be used in applications where the presence of a retinoid is desirable. Typically, the retinoid containing composition can be used in topical applications where the retinoid containing composition is applied to skin tissue. In the case of drug applications, the retinoid containing composition can be used to treat acne, psoriasis, and skin cancer. A retinoid containing composition can be used in cosmetic applications (e.g., as a cosmetic composition) because of the beneficial properties retinoids provide relating to cell turnover and renewal. Retinoid containing compositions that are used as drug compositions tend to be regulated whereas cosmetic compositions are generally not regulated. As a result, there is typically a difference between retinoid containing compositions that are considered a drug composition and retinoid compositions that are considered a cosmetic composition.

The retinoid containing composition can provide enhanced retinoid stability to visible light and oxygen compared with commonly available retinoid containing compositions that are used in either or both of drug applications and cosmetic applications. Furthermore, the retinoid stability can be provided without the need to formulate the composition in the presence of a special light (e.g., a yellow light) and without the need for a blanket of inert gas (e.g., nitrogen or argon). Commonly available retinoid containing compositions are produced under a yellow light and under a blanket of inert gas to reduce the degradation of the retinoid. In addition, the compositions are typically packaged in an opaque container and under a blanket of inert gas. Once the container is opened, the composition is exposed to both light and oxygen, and the retinoid can begin degrading thereby resulting in loss of efficacy over time. The retinoid containing composition according to the invention can be prepared under normal light (e.g., visible light) and exposed to air without the need for a blanket of inert gas. In addition, the retinoid containing composition according to the invention can be packaged without the need for an inert gas, and once the container is opened, the retinoid containing composition can provide a desired level of retinoid activity over time. That is, even after exposure to visible light and oxygen, the efficacy of the retinoid containing composition can remain as a result of the enhanced stabilization of the retinoid. Furthermore, the retinoid containing composition can be packaged under an oxygen containing atmosphere (without a blanket of inert gas), and the resulting packaged retinoid containing composition can provide a desired level of stability.

The retinoid containing composition can be provided so that it has a desired level of stability. When packaged in an opaque container under an oxygen atmosphere (e.g., air), the retinoid can retain about 70% of its original activity after accelerated stability testing at 40° C. for 120 days. Preferably, the retinoid can retain about 80% of its original activity, and more preferably at least about 90% of its original activity after accelerated stability testing at 40° C. for 120 days. It should be understood that it is the packaged retinoid containing composition that can be stability tested. The packaged retinoid containing composition can contain an opaque container sealed against the atmosphere but packaged under an oxygen atmosphere. This enhanced stability can be achieved without the need for formulating the composition under a yellow light and an inert gas.

The retinoid containing composition can be provided in the form of a lotion, cream, gel, or liquid and applied to skin tissue by rubbing the composition onto the skin tissue. The retinoid containing composition can have a viscosity that allows it to be applied to skin tissue conveniently as a lotion, cream, gel, or liquid. The retinoid containing composition can have a viscosity that is sufficiently high so that the lotion can be applied from a container (e.g., a tube or a bottle) to a person's hand or a location on the person's body, and the lotion can be rubbed onto the skin tissue. When provided as a lotion, cream, or gel, the retinoid containing composition can have a viscosity of greater than about 3,000 cSt (centistokes). The retinoid containing composition can be provided in a form having a viscosity of less than about 3,000 cSt. When the retinoid containing composition is provided having a viscosity of less than about 3,000 cSt, the retinoid containing composition can be referred to as a liquid.

The retinoid containing composition includes a retinoid component, a hydrophobic polymer/hydrophilic polymer adduct, and water. In drug compositions, retinoids are typically used as the sole active ingredient. One reason for this is that retinoids are typically unstable and have a tendency to degrade in the presence of other active ingredients. The retinoid containing composition according to the invention, when provided as a drug composition, can include additional active ingredients, if desired. Because of the enhanced stability of the retinoid provided by the present invention, additional active ingredients can be included, if desired, without significant degradation of the retinoid. In the case of cosmetic compositions, multiple active ingredients are commonly used, and it is expected that a retinoid will be used in combination with one or more additional active ingredients. Again, the retinoid containing composition according to the invention enhances the stability of the retinoid so that it can remain stable even after exposure to other active ingredients in a cosmetic composition. In addition, the retinoid containing composition can include a release agent to provide a sustained release of the retinoid or the active agent over a prolonged period of time. The release agent can be a surfactant. The retinoid containing composition can be provided without a release agent (for example, without a surfactant). Additional components that can be included or excluded from the composition include pH modifying agents, coloring agents, preservatives, thickening agents, emollients, humectants, antioxidants, fragrances, and chelating agents.

The retinoid containing composition can be provided as an emulsion. Exemplary types of emulsions include oil in water emulsions, and water in oil in water emulsions.

Retinoid

Retinoids are typically characterized as a class of chemical compounds that are related to vitamin A. In general, retinoids include all natural and/or synthetic analogs of vitamin A or retinol-like compounds which possess the biological activity of vitamin A in the skin as well as the geometric isomers and stereoisomers of these compounds.

Retinoids are also useful in providing unexpected benefits in regulating skin conditions, especially in therapeutically regulating signs of skin ageing, more especially wrinkles, lines, and pores. The retinoids for this benefit can include retinol, retinol esters (e.g., $C_2$-$C_{22}$ alkyl esters of retinol, including retinyl palmitate, retinyl acetate, retinyl propionate), retinal, and retinoic acid (including trans retinoic acids and 13-cis-retinoic acids). These compounds are well know in the art and are commercially available from a number of sources, such as, Sigma Chemical Company (St. Louis, Mo.) and Boerhinger Mannheim (Indianapolis, Ind.). Other retinoids which are useful herein are described in U.S. Pat. Nos. 4,677,120, issued Jun. 30, 1987 to Parish et al.; 4,885,311, issued Dec. 5, 1989 to Parish et al.; 5,049,584, issued Sep. 17, 1991 to Purcell et al.; 5,124,356, issued Jun. 23, 1992 to Purcell et al; and Reissue 34,075, issued Sep. 22, 1992 to Purcell et al. Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). One or more retinoids may be used in combination. Exemplary retinoids include retinol, retinyl palmitate, retinyl acetate, retinyl propionate, retinal and combinations thereof. More preferred are retinol and retinyl propionate.

The retinoid may be provided as a substantially pure material, or as an extract obtained by suitable physical and/or chemical isolation from natural (e.g., plant) sources.

Retinoids are used in medicine, primarily due to the way they regulate epithelial cell growth. In general, retinoids have been found to function in vision, regulation of cell proliferation and differentiation, growth of bone tissue, immune function, and activation of tumor suppressor genes. Retinoids are commonly linked to the potential treatment of skin cancers. Various types of retinoids are available. Exemplary, retinoids include ritinol, retinal, tretinoin (retin-A), isotretinoin, alitretinoin, etretinate, acitretin, tazarotene, vexarotene, and adapalene.

Retinoic acid can be referred to under its common name tretinoin, and has the following structure:

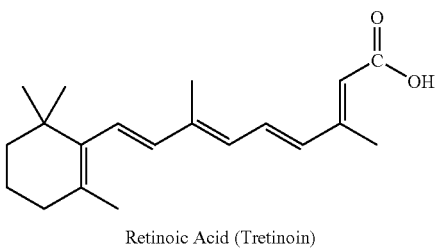

Retinoic Acid (Tretinoin)

The structure of retinol is:

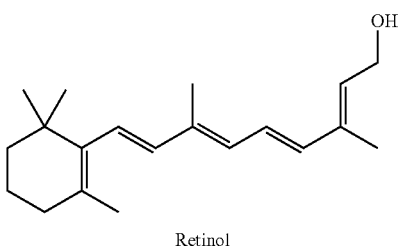

Retinol

Retinoic acid is often used as a pharmaceutical grade of retinoic acid for drug compositions. Exemplary forms of retinoic acid are disclosed in, for example, U.S. Pat. No. 3,729,568 and U.S. Pat. No. 4,126,699, the disclosures of which is incorporated herein by reference. Adapalene is considered a topical retinoid, and is available under the name Differin® from Galderma. Other topical retinoids can be used, if desired.

Various amounts of retinoid can be provided in the retinoid containing composition. In general, the amount of retinoid in a retinoid containing composition depends on the activity of the retinoid. Certain retinoids are very active and, as a result, relatively small amounts of those retinoids can be used. Other retinoids are less active and as a result, larger amount of those retinoids can be used. In general, retinoids can be used in an amount of about 0.0001 wt. % to about 5 wt. %, preferably about 0.001 wt. % to about 5 wt. %, and more preferably about, 0.01 wt. % to about 3 wt. %. In the case of retinoic acid, the amount of retinoic acid in a retinoid containing composition can be about 0.01 wt. % to about 0.15 wt. %, and can be about 0.025 wt. % to about 0.1 wt. %. Various cosmetic compositions, however, can contain about 0.01 wt. % to about 2 wt. %, and preferably about 0.05 wt. % to about 1 wt. % of a retinoid such as a cosmetic grade retinoid (e.g., retinol).

Polymer Component

The retinoid containing composition can include a polymer component that protects the retinoid from degradation as a result of exposure to visible light, an oxygen containing atmosphere or both visible light and an oxygen containing atmosphere. The polymer component can be provided as a component that exhibits a tendency to bond to skin tissue. When the polymer component is provided as a polymer that has a tendency to bond to skin tissues, the polymer component can be characterized as a skin bonding polymer component, in general, the polymer component can be provided as a polymer having an average molecular weight of at least about 2,000, an as polymer having an average molecular weight about 500,000.

The polymer component can include a hydrophobic polymer/hydrophilic polymer adduct and can include other components. Polymer components that can be used according to the invention include the topical compositions disclosed in U.S. Pat. No. 6,756,059. The entire disclosure of U.S. Pat. No. 6,756,059 is incorporated herein by reference.

The polymer component of the retinoid containing composition is believed responsible for holding on to or isolating the retinoid to preserve the stability of the retinoid. In general, retinoids include unsaturation (e.g., conjugated unsaturation), and light and oxygen have a tendency to alter the unsaturation thereby resulting in loss of activity. It is believed that the polymer component helps preserve the retinoid from degradation as a result of exposure to light, oxygen, or both. The precise mechanism of this enhanced stability is not fully known. The enhanced stability, however, is observed as reported in the example. In addition, the polymer component can help hold the retinoid in proximity to the skin tissue once it is applied to skin tissue. By binding to skin tissue and holding on to the retinoid, the polymer component can help deliver the retinoid to the skin tissue to provide a desired level of activity for a desired length of time. For example, the retinoid containing composition can be provided so that it adheres or binds to skin tissue for at least about one hour, and preferably about two hours, and holds the retinoid in proximity to the skin tissue for that length of time.

The polymer component can be prepared from a topical composition precursor. The topical composition precursor can be prepared by melt processing a hydrophobic polymer composition and a hydrophilic polymer composition to provide an interaction between the hydrophobic polymer composition and the hydrophilic polymer composition. It should be understood that the phrase "melt processing" refers to mixing the hydrophobic polymer composition and the hydrophilic polymer composition under conditions that provide that the hydrophobic polymer component of the hydrophobic polymer composition and the hydrophilic polymer component of the hydrophilic polymer composition are in a liquid state so that they sufficiently mix. When the polymers are sufficiently mixed, it is believed that an interaction forms between the hydrophobic polymer component and the hydrophilic polymer component. The melt processing temperature can be at least about 50° C. and can be at least about 70° C. to generate this interaction.

It is theorized that the interaction exhibited between the hydrophobic polymer component and the hydrophilic polymer component is a type of complex formation reaction, and that the complex, once formed, can be stable in water at temperatures up to 65° C. and at a pH range of 3.0 to 9.0. By stable, it is meant that the complex does not favor disassociation under these conditions. It is believed that this interaction provides the retinoid containing composition with an ability to bind or hold onto the retinoid component that may be hydrophobic or relatively water insoluble while protecting the retinoid from degradation, allows the composition to be emulsified in water, and provides the retinoid containing composition with an ability to bind to skin. The result of the interaction between the hydrophobic polymer component and the hydrophilic polymer component can be referred to as a hydrophobic polymer/hydrophilic polymer adduct. It should be understood that the term "adduct" is used to refer to the interaction between the hydrophobic polymer component and the hydrophilic polymer component. The interaction may be a form of complexing, but that is only theory. Accordingly, it should be understood that the term "adduct" is not meant to limit the polymer component to a particular theory of interaction.

It is believed that the interaction between the hydrophobic polymer component and the hydrophilic polymer component can be achieved more easily in the absence of water. It is expected that that if the hydrophilic polymer component becomes dissolved in water before forming the complex, it can be more difficult to sufficiently mix the hydrophobic polymer component and the hydrophilic polymer component to provide the desired level of interaction. Although a convenient technique for providing the desired level of interaction between the hydrophobic polymer component and the hydrophilic polymer component is melt mixing, it is expected that other techniques can be used to achieve the desired level of interaction. For example, it may be possible to use a nonaqueous solvent to help achieve the desired level of interaction.

The hydrophobic polymer composition that can be used according to the invention includes at least one hydrophobic polymer and can include a mixture of hydrophobic polymers. The hydrophobic polymer composition can include components having repeating pyrrolidone/alkylene groups. Exemplary polymers having repeating pyrrolidone/alkylene groups include poly(vinylpyrrolidone/alkylene) polymers. Poly(vinylpyrrolidone/alkylene) polymers include those polymers obtained by polymerizing alkylene substituted vinylpyrrolidone. Poly(vinylpyrrolidone/alkylene) polymers can be represented by the following general formula:

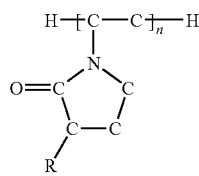

wherein R represents a carbon chain substitute such as an alkylene group and n represents the number of repeating units. The R group is preferably sufficiently long so that the polymer remains relatively water insoluble and should not be too long so that the polymer is difficult to melt process. The alkylene group can contain a length of at least about 10 carbon atoms and can contain less than about 30 carbon atoms. The alkylene group can contain about 14 carbon atoms to about 22 carbon atoms, and can contain about 15 carbon atoms to about 19 carbon atoms.

The poly(vinylpyrrolidone/alkylene) polymers that can be used according to the invention can have a molecular weight that is sufficiently high so that the polymer maintains its water insolubility but the molecular weight should not be so high that it becomes difficult to melt process the polymer. The weight average molecular weight of the poly(vinylpyrrolidone/alkylene) polymer can be between about 3,000 and about 400,000. Another way to characterize the size of the poly(vinylpyrrolidone/alkylene) polymer is by the number of repeating units (n). In the case of a poly(vinylpyrrolidone/alkylene) polymer having a weight average molecular weight of about 6,000 to about 30,000, the poly(vinylpyrrolidone/alkylene) polymer can have about 20 to about 80 repeating units, and can have about 30 to about 50 repeating units. It should be understood that repeating units refer to the residues of vinylpyrrolidone/alkylene groups.

Exemplary poly(vinylpyrrolidone/alkylene) polymers that can be used according to the invention include poly(vinylpyrrolidone/1-eicosene) and poly(vinylpyrrolidone/hexadecene). Poly(vinylpyrrolidone/1-eicosene) can be referred to as PVPE and is commonly used in pharmaceutical and cosmetic preparations. An exemplary form of PVPE for use according to the invention includes about 43 to 44 repeating units in length and has a weight average molecular weight of about 17,000 and can be characterized as a paraffin-like solid. This particular PVPE is highly insoluble in water, and has an extremely low oral toxicity ($LD_{50}$>17000 mg/kg) and exhibits no demonstrable dermal toxicity. Poly(vinylpyrrolidone/1-hexadecene) can be referred to as PVPH. An exemplary form of PVPH is available as a viscous yellow liquid that is insoluble in water and has a low oral toxicity ($LD_{50}$>64000 mg/kg), has about 39 to 40 repeating units, a molecular weight of about 14,000, and exhibits no demonstrable dermal toxicity.

PVPE and PVPH differ in the length of the hydrocarbon side chain, and are used extensively in the skin care industry, usually in concentrations of less than 1% by weight, because of their ability to bind to skin. Because the skin care industry generally prefers to apply actives to skin using a water-based composition, the use of PVPE and PVPH often requires solvents, surfactants, and emulsifiers to stabilize these polymers in a water emulsion. However, many of the solvents, surfactants and emulsifiers used to stabilize PVPE and PVPH in a water emulsion lack the low dermal toxicities of PVPE and PVPH. PVPE and PVPH by themselves lack a cosmetically elegant appeal when applied directly to the skin. They tend to be sticky and greasy.

The hydrophobic polymer composition used according to the invention can be provided as a mixture of different poly(vinylpyrrolidone/alkylene) polymers. The mixture of different poly(vinylpyrrolidone/alkylene) polymers can include at least 5 wt. % of a first poly(vinylpyrrolidone/alkylene) polymer based on the weight of the hydrophobic polymer composition. The hydrophobic polymer composition can include about 5 wt. % to about 54 wt. % of the first poly(vinylpyrrolidone/alkylene) polymer. The second poly(vinylpyrrolidone/alkylene) polymer can be provided in an amount of at least about 46 wt. % and can be in a range of about 46 wt. % to 95 wt. % based on the weight of the hydrophobic polymer composition. For a hydrophobic polymer composition containing a first poly(vinylpyrrolidone/alkylene) polymer and a second poly(vinylpyrrolidone/alkylene) polymer, the mole ratio of the first polymer to the second polymer can be about 1:22 to about 1:1. When the hydrophobic polymer composition contains a mixture of different poly(vinylpyrrolidone/alkylene) polymers, the poly(vinylpyrrolidone/alkylene) polymers can be selected to provide improved properties compared to a composition having a hydrophobic polymer composition containing a single poly(vinylpyrrolidone/alkylene) polymer.

When the hydrophobic polymer composition is provided as a mixture of PVPH and PVPE, the PVPH can be provided in a range of about 46 wt. % to about 95 wt. % and the PVPE can be provided in a range of about 5 wt. % to about 65 wt. %, based upon the weight of the hydrophobic polymer composition.

The hydrophilic polymer composition that can be used according to the invention includes at least one hydrophilic polymer and may include a mixture of hydrophilic polymers. The hydrophilic polymers that can be used according to the invention include polymers having repeating carboxylic acid groups, hydroxyl groups, or both carboxylic acid groups and hydroxyl groups. Exemplary hydrophilic polymers that can be used according to the invention include polyacrylic acid polymers, poly(maleic acid/methylvinylether) copolymers, starch, derivatives of starch, polyvinyl alcohol, cellulose, derivatives of cellulose, carboxymethyl cellulose, cyclodextrins, dextrans, or mixtures thereof. The hydrophilic polymers should have a molecular weight that is not too high so that the hydrophilic polymer becomes difficult to process.

Polyacrylic acid polymers that can be used according to the invention include those having a weight average molecular weight of at least about 50,000. Polyacrylic acid polymers that can be used include those having a weight average molecular weight between about 50,000 to about 4,000,000. The polyacrylic acid polymers can have a level of cross-linking that is less than about 1% to help provide hydrophilic properties. A general structural representation of polyacrylic acid polymers is shown below:

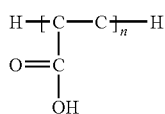

wherein n is the number of repeating units. The number n can be about 1,000 to about 20,000.

Poly(maleic acid/methylvinylether) copolymers that can be used according to the invention can have a weight average molecular weight of at least about 50,000, and can have a weight average molecular weight of about 50,000 to about 4,000,000. The weight average molecular weight can be about 70,000 to 2,500,000. A general structural representation of poly(maleic acid/methylvinylether) copolymers is shown below:

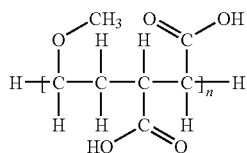

wherein n is the number of repeating units. The number n can be about 200 to about 20,000.

Additional hydrophilic polymers that can be used according to the invention include starch, derivatives of starch, polyvinyl alcohol, cellulose, derivatives of cellulose, carboxymethyl cellulose, cyclodextrins, and dextrans. The weight average molecular weight of the hydrophilic polymers is preferably sufficient to provide solubility in water but not too high to become difficult to process. Exemplary starches include amylopectin and polyglucose. Starches that can be used according to the invention can have a weight average molecular weight of about 50,000 to about 20,000,000. An exemplary starch component that can be used includes *Zea Mays* starch. A derivative of starch that can be used according to the invention includes partially hydrolyzed starch. Cellulose that can be used according to the invention can have a weight average molecular weight of about 50,000 to about 15,000,000. An exemplary cellulose component that can be used includes cellulose gum. Polyglucose that can be used according to the invention can be characterized as low fraction polyglucose having a weight average molecular weight of about 60,000 to about 90,000, and high fraction polyglucose having a weight average molecular weight of about 90,000 to about 300,000. An exemplary low fraction polyglucose material that can be used according to the invention is available under the name Dextran-70. In general, this type of polyglucose has all alpha 1-6 linkages. Starch derivatives that can be used according to the invention include those starch derivatives having alpha 1-4 linkages. An example of this type of starch derivative includes cyclodextrins. Exemplary cyclodextrins that can be used according to the invention include those that act to provide a cavity within the molecule large enough to contain components desirable for topical applications. Cyclodextrins that can be used according to the invention can have a molecular weight of about 900 to about 1,400. Polyvinyl alcohols that can be used according to the invention include those with a weight average molecular weight of about 50,000 to about 200,000.

Exemplary hydrophilic polymers that can be used according to the invention include those polymers having a melting temperature that allows for melt processing without decomposition of the polymer. Exemplary poly(maleic acid/methylvinylether) copolymers that can be used include those having a melting temperature range of about 60° C. to about 65° C. and a maximum temperature range of about 80° C. to about 90° C. The melting temperature refers to the temperature at which the polymer melts, and the maximum temperature refers to the temperature at which the polymer begins to decompose. Exemplary polyacrylic acid polymers that can be used include those having a melting temperature range of about 65° C. to about 70° C. and a maximum temperature range of about 80° C. to about 90° C. Exemplary carboxymethyl cellulose polymers that can be used include those having a melting temperature range of about 55° C. to about 60° C. and a maximum temperature range of about 75° C. to about 80° C. Exemplary polyvinyl alcohol polymers that can be used include those having a melting temperature range of about 50° C. to about 55° C. and a maximum temperature range of about 65° C. to about 70° C. Exemplary starches that can be used include those having a melting temperature range of about 40° C. to about 45° C. and a maximum temperature range of about 50° C. to about 55° C. Exemplary dextrans that can be used include those having a melting temperature range of about 37° C. to about 40° C. and a maximum temperature range of about 45° C. to about 50° C. Exemplary β-cyclodextrins that can be used according to the invention include those having a melting temperature range of about 40° C. to about 45° C. and a maximum temperature range of about 65° C. to about 70° C.

The hydrophobic polymer composition and the hydrophilic polymer composition can be combined and heated to at least about 50° C. to provide a polymer melt. The composition can be heated to at least about 70° C. under mixing to form complexes between the hydrophobic and hydrophilic polymers. It should be understood that a polymer melt refers to a polymer that flows or becomes a liquid when heated and is not meant to refer to a polymer that forms a liquid as a result of being dissolved in a solvent.

The complex formation step can be carried out in a relatively anhydrous environment. That is, the amount of water provided in the composition during the complex formation step can be less than about 1 wt. %. Once the desired level of complex formation has occurred, the composition can be hydrated with water.

The hydrophobic polymer composition and the hydrophilic polymer composition can be mixed together in amounts sufficient to provide a ratio of pyrrolidone groups to the combination of carboxylic acid groups and hydroxyl groups of about 1:1 to about 5:1. The ratio of the structures causing the observed interaction between the hydrophobic polymer composition and the hydrophilic polymer composition can be referred to as "functional group parity." The ratio of pyrrolidone groups to the combination of carboxylic acid groups and hydroxyl groups can be about 1.5:1 to about 3:1. In order to drive the complex formation reaction, it is desirable to provide an imbalance between the two types of groups.

Accordingly, it is generally desirable to provide more of the pyrrolidone groups than the combination of carboxylic groups and the hydroxyl groups. It should be understood that the reference to a "combination of carboxylic groups and hydroxyl groups" refers to the total amount of carboxylic groups and hydroxyl groups present but does not require the presence of both carboxylic groups and hydroxyl groups. For example, the value of the combination of carboxylic groups and hydroxyl groups can be determined for a composition that contains only carboxylic groups. Similarly, the value can be determined for a composition that contains only hydroxyl groups.

During the complex formation step, the amounts of hydrophobic polymer composition and hydrophilic polymer composition can be characterized on a weight percent basis. For example, about 2 wt. % to about 28 wt. % hydrophilic polymer composition and about 72 wt. % to about 98 wt. % hydrophobic polymer composition can be combined to provide for complex formation. About 8 wt. % to about 25 wt. % hydrophilic polymer composition and about 72 wt. % to about 95 wt. % hydrophobic polymer composition can be combined to form the complex. During the complex formation step, the amount of water available in the composition can be less than about 1 wt. %. Although the complex forming composition can be relatively anhydrous, it is expected that the amount of water will be between about 0.3 wt. % and about 1.0 wt. %.

Once the hydrophobic polymers and the hydrophilic polymers have sufficiently reacted or interacted to form a complex, water can be added to the composition to provide a stable aqueous composition that can be relatively easily further hydrated. It has been found that the first hydration of the topical composition precursor is the most difficult hydration step because of the need to control the conditions of hydration. After the first hydration to a water content of at least about 30 wt. %, it is expected that further hydrations to higher water contents are relatively easy and can be accomplished by simply mixing the composition with water. Accordingly, the amount of water provided in the composition when made available as a concentrate for shipment is preferably between about 30 wt. % and about 45 wt. %. When the composition includes about 30 wt. % to about 45 wt. % water, it is expected that the composition can include about 3 wt. % to about 10 wt. % hydrophilic polymer composition and about 30 wt. % to about 50 wt. % hydrophobic polymer composition.

Water can be added to the relatively anhydrous composition by mixing water and the relatively anhydrous composition at a temperature and for a time sufficient to allow the composition to become hydrated without losing significant amounts of interaction between the hydrophobic polymer composition and the hydrophilic polymer composition. The relatively anhydrous composition can be hydrated by heating to at least 60° C. and adding water while mixing. The composition can be heated to at least about 65° C. and to at least about 70° C. An exemplary temperature range is about 65° C. to about 80° C.

The relatively anhydrous composition can be referred to as the topical composition precursor and generally refers to the hydrophobic polymer/hydrophilic polymer adduct. The polymer component for the composition can refer to a composition that contains only the hydrophobic polymer/hydrophilic polymer adduct, and it can refer to a composition wherein the hydrophobic polymer/hydrophilic polymer adduct is diluted with water. In general, it is desirable to have a sufficient amount of water in the polymer component that allows one to formulate the polymer component into the composition according to the invention. If there is too little water in the polymer component, it may become difficult to formulate the composition. For example, the polymer component can contain water in an amount of up to about 95 wt. %. The polymer component can have a water concentration of about 30 wt. % to about 45 wt. %.

Additional components can be added to the hydrophobic polymer/hydrophilic polymer adduct. For example, it may be desirable to add a component that helps stabilize the hydrophobic polymer/hydrophilic polymer adduct, and to help preserve and/or maintain the composition.

The retinoid containing composition can include the polymer component in an amount sufficient to provide desired bonding properties of the composition. For example, the retinoid containing composition can include at least about 3 wt. % of the polymer component, and preferably at least about 4 wt. % of the polymer component. In addition, the retinoid containing composition can include a sufficient amount of the polymer component to desirably protect the retinoid from degradation and allow the retinoid containing composition to deliver the retinoid to skin tissue upon application of the retinoid containing composition to skin tissue. The retinoid containing composition can contain the polymer component in an amount of less than about 20 wt. %, and preferably in an amount of less than about 15 wt. %. A preferred range of polymer component can be about 5 wt. % to about 8 wt. %.

An exemplary polymer component that can be used is available under the name Invisicare C-5 from Skinvisible Pharmaceuticals, Inc. The Invisicare C-5 polymer can be characterized as a polymer adduct containing about 40 wt. % water and about 60 wt. % polymer adduct prepared from carboxymethyl cellulose and a mixture of poly(vinylpyrrolidone/1-eicosene) and poly(vinylpyrrolidone/hexadecene).

The mechanism for stabilizing the retinoid as a result of the presence of the hydrophobic polymer/hydrophilic polymer adduct is not fully understood. It is theorized, however, that the aliphatic chains of the polyvinylpyrrolidone groups somehow interact to protect the retinoid from attack by oxygen or light. An exemplary characterization of the relationship between retinoic acid and polyvinylpyrrolidone is shown by the following chemical formula. Furthermore, it is expected that the polyvinylpyrrolidone can form a 3-dimensional network to surround the retinoid and protect the retinoid. Data presented in the examples demonstrates a stabilizing affect on retinoic acid as a result of the presence of the hydrophobic polymer/hydrophilic polymer adduct provided as the Invisicare C-5 polymer from Skinvisible Pharmaceuticals, Inc. A similar stabilizing effect, however, was not observed for retinol and retinyl palmitate utilizing the same polymer adduct. Accordingly, there may be some other theory that supports the observation of a stabilizing affect on retinoic acid but a lack of stabilizing affect on retinol and retinyl palmitate. Although a stabilizing effect on retinol and retinyl palmitate was not observed using the Invisicare C-5 polymer, there may be other retinoids that are stabilized similar to the stabilization of retinoic acid. If desired, one can characterize the existence of a stabilizing effect, based on the presence of the hydrophobic polymer/hydrophilic polymer adduct, on retinoids excluding retinol and retinyl palmitate. Also, there may be other polymer adducts that stabilize retinoids in addition to retinoic acid (i.e., retinol and retinyl palmitate).

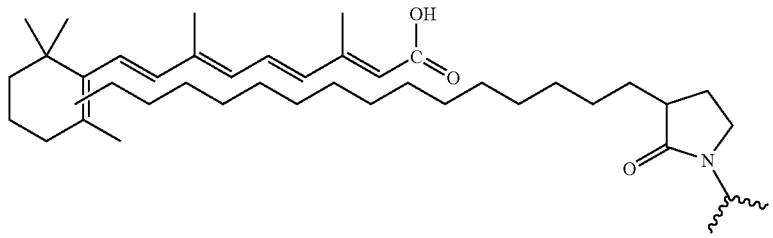

Water

The retinoid containing composition can include water in an amount sufficient to allow the composition to be applied to skin tissue while providing the desired coverage over the skin tissue. The water component can be provided as deionized water, filtered water, distilled water, reverse osmosis water, or tap water. In the event that the water includes hardness or other components, it may be desirable to include builders, sequestrants, and chelating agents to handle the water hardness. In general, the retinoid containing composition can include at least about 50 wt. % water. In addition, it is expected that if there is too much water, the emulsion might become unstable. In general, the amount of water in the retinoid containing composition can be less than about 95 wt. %. The amount of water in the retinoid containing composition can be about 65 wt. % to about 93 wt. %.

Release Agent

The retinoid containing composition can include a release agent to assist with the sustained release of the retinoid over a prolonged period of time. The release agent can be provided as a surfactant. A surfactant can additionally be present to help maintain the retinoid containing composition as an emulsion. In general, an emulsion refers to a composition that resists phase separation after sitting at room temperature for a couple of months. In general, it is expected that the retinoid containing composition can be stored in a warehouse or in a storage closet for at least two months and can remain as an emulsion during that two month period. Preferably, the retinoid containing composition can remain as an emulsion for at least one year or at least two years. The ability of the retinoid containing composition to remain as an emulsion can be tested according to an accelerated stability test where the composition is held at 40° C. for 120 days. It is expected that this accelerated stability test for 120 days roughly corresponds to a period of about two years at room temperature. In general, it is expected that the retinoid containing composition can remain as an emulsion after sitting for two years at room temperature.

Exemplary surfactants that can be used as the surfactant component include nonionic surfactants that help stabilize the emulsion and provide a generally even distribution of the retinoid containing component. Exemplary nonionic surfactants that can be used include glycerol stearate such as glycerol monostearate, polysorbate such as that available under the name Tween 80, polyoxyethylene stearate. In addition, mixtures of nonionic surfactants can be included including mixtures of polysorbate and glycerol stearate. An additional nonionic surfactant that can be used includes an ethoxy surfactant, a propoxy surfactant, or an ethoxy/propoxy surfactant. An exemplary ethoxy/propoxy surfactant includes a 10 carbon chain and 9 PO/EO surfactant available under the name Lutensol XP-90 from BASF. Additional nonionic surfactants include sorbitan monolaurate and sorbitan monostearate. Additional surfactants that can be used include those that are generally characterized as Pluronic surfactants such as poloxamers. An exemplary surfactant that can be used is Pluronic P 123 from BASF.

It is believed that anionic surfactants may be useful as part of the surfactant component. In general, it is expected that anionic surfactants have a greater tendency to cause irritation to skin tissue.

The retinoid containing composition can include an amount of surfactant component sufficient to provide the composition with a desired emulsion stability and sufficiently low viscosity without foaming. The amount of the surfactant component in the retinoid containing composition, can be about 0.5 wt. % to about 6 wt. %, and can be about 1 wt. % to about 5 wt. %. It should be understood that the retinoid containing composition can be provided without any surfactant component, if desired.

The retinoid containing composition can contain a release agent to assist with the sustained release of the retinoid over a prolonged period of time. A sustained release of the retinoid component refers to a release, over the time period, wherein the release provides desired properties. In general, it is desirable for the retinoid containing composition to provide a relatively consistent release of the retinoid component after application of the composition to skin tissue. A relatively consistent release can be characterized as a release rate at one hour that is within about 50% of the release rate at 30 minutes. In addition, a relatively consistent release rate can be characterized as a release rate at two hours that is within about 50% of the release rate at 30 minutes. Preferably, these release rates can be provided within about 25%, and more preferably can be provided within about 15%.

At least two advantages can be obtained by providing a sustained release rate or a relatively constant release rate over a prolonged period of time. For example, by providing a sustained release of the retinoid over a prolonged period of time, it is possible to prolong the pharmaceutical efficacy of the retinoid containing composition after application to skin tissue. By prolonging the pharmaceutical efficacy of the retinoid containing composition, it is expected that enhanced performance can be achieved. Furthermore, by controlling the release of the retinoid so that it is not released at one instant in time, it is possible to reduce or minimize skin irritation. Many retinoids have a tendency to cause skin irritation if provided at a concentration that is too high. By controlling the release of the retinoid, it is possible to reduce the tendency of the retinoid to cause skin irritation because too much of it is released at one time.

pH Adjusting Agent

The retinoid containing composition can include a pH adjusting agent or neutralizing agent to provide the retinoid containing composition with a pH that helps stabilize the retinoid containing component. Exemplary pH adjusting agents that can be used include sodium hydroxide, potassium hydroxide, triethanolamine, and mixtures thereof.

The polymer component of the lotion, cream, gel, or liquid may be at least in part responsible for reducing the irritability of the retinoid containing composition. For example, it is believed that the polymer component may help reduce irritation of skin tissue. The retinoid containing composition can be provided without any pH modifier, if desired.

Thickener

Thickeners that can be incorporated into the retinoid containing composition include those components that thicken or increase the viscosity of the retinoid containing composition so that the retinoid containing composition can be readily applied to skin. Thickeners that can be used in the retinoid containing composition include those components often referred to as viscosity controlling agents.

Exemplary thickeners or viscosity controlling agents that can be provided in the hand disinfecting composition include cellulose gum, alkane triols; acrylates; substituted celluloses such as hydroxy ethyl cellulose, carboxymethyl cellulose, methylcellulose, and hydroxypropyl cellulose; cetyl alcohol; gums such as natural gums or synthetic gums; long chain alcohols such as those having about 9 to about 24 carbon atoms; polyglycols such as polyethylene glycols, polypropylene glycols, polybutylene glycols, polyethylene propylene glycols, or mixtures thereof; waxes such as natural waxes or synthetic waxes; hydrogenated oils; glycol esters; fatty acid esters; long chain acids; acid amides; silicates; and mixtures thereof. An exemplary thickener that can be used is hydroxyethyl cellulose. An exemplary thickener that can be used is a polyacrylic acid thickener available under the name Carbopol U-10 from Lipscomb.

The retinoid containing composition may or may not include a thickener. When the retinoid containing composition includes a thickener, the thickener can be provided in an amount that provides the desired level of thickening. The retinoid containing composition can include a thickener in an amount of least about 0.1 wt. % and can include a thickener in an amount of at least about 0.4 wt. %. In addition, the thickener can be provided in an amount of less than about 2 wt. %, and can be provided in an amount of less than about 1.0 wt. %.

Emollient

The retinoid containing composition can include an emollient for improving the texture of the composition. An emollient is an oleaginous or oily substance which helps to smooth and soften the skin, and may also reduce its roughness, cracking or irritation. Exemplary suitable emollients include mineral oil, having a viscosity in the range of 50 to 500 centipoise (cps), lanolin oil, coconut oil, cocoa butter, olive oil, almond oil, macadamia nut oil, synthetic jojoba oils, natural sonora jojoba oils, safflower oil, corn oil, liquid lanolin, aloe vera, cottonseed oil, and peanut oil.

Other suitable emollients include squalane, castor oil, polybutene, odorless mineral spirits, sweet almond oil, avocado oil, clophyllum oil, ricin oil, vitamin E acetate, olive oil, linolenic alcohol, coconut oil, oleyl alcohol, the oil of cereal germs such as the oil of wheat germ, isopropyl palmitate, isopropyl myristate, hexadecyl stearate, butyl stearate, decyl oleate, acetyl glycerides, the octanoates and benzoates of ($C_{12}$-$C_{15}$) alcohols, the octanoates and decanoates of alcohols and polyalcohols such as those of glycol and glycerol, ricin oleates of alcohols and poly alcohols such as those of isopropyl adipate, hexyl laurate and octyl dodecanoate.

Other suitable emollients which are solids or semi-solids at room or ambient temperatures may be used in amounts sufficient to provide liquid topical compositions. Such solid or semi-solid cosmetic emollients include hydrogenated lanolin, hydroxylated lanolin, acetylated lanolin, petrolatum, isopropyl lanolate, butyl myristate, cetyl myristate, myristyl myrislate, myristyl lactate, cetyl alcohol, isostearyl alcohol and isocetyl lanolate. Exemplary emollients include stearic acid, stearyl alcohol, palmitic acid enters natural and synthetic esters such as coconut oil.

The retinoid containing composition can include the emollient in an amount sufficient to provide a silky feel. An exemplary range of the emollient in the composition can be at least about 0.5 wt. %. In addition, the composition can include an emollient in an amount of less than about 3 wt. %. It should be understood that the emollient is an optional component of the composition. The retinoid containing composition can be provided without an emollient, if desired.

Moisturizer

The retinoid containing composition can include a moisturizer to provide a desired moisturizing effect to skin tissue. The moisturizer can be provided as a humectant. In general, a humectant is a moistening agent that promotes retention of water due to its hydroscopic properties. Exemplary humectants include glycerine, polymeric glycols such as polyethylene glycol and polypropylene glycol, and sorbitols such as sorbitol solution, pyrrolidone carboxylic acid, urea, or mixtures thereof. The retinoid containing composition can be provided without a moisturizer.

When the retinoid containing composition includes a moisturizer, it can be included in an amount of at least about 0.5 wt. %. In addition, the retinoid containing composition can include a moisturizer in an amount of less than about 5 wt. %.

An additional component that can be provided as part of the retinoid containing composition is a skin protectant. An exemplary protectant is allontoin that is available as a skin protectant and esthetic agent.

Preservatives

The retinoid containing composition can include preservatives for prevention of bacterial, fungal, and/or yeast contamination. Exemplary preservatives that can be used in the hand disinfecting composition include phenoxyethanol, benzoic acid, derivatives and salts of benzoic acid, parabens, oxazolidines, chlorinated aromatic compounds and phenols, hydantoins, cresols and derivatives, imiazolindinyl urea, iodopropanol butylcarbamate, sulfites, and bisulfites. The retinoid containing composition can include any of the preservatives commonly used or known to be suitable for topically applied compositions. Exemplary commercially available preservatives include liquid Germal Plus (diazolidinyl urea and iodopropynyl butylcarbamate) and Germaben 11 (diazolidinyl urea and methylparaben and propylparaben).

The retinoid containing composition can be formulated without a preservative. It is expected that the preservative will increase the shelf life of the retinoid containing composition by reducing or preventing the growth of bacteria, fungus, and/or yeast. When the retinoid containing composition includes a preservative, the preservative is preferably provided in an amount sufficient to provide a desired level of protection from growth of bacteria, fungus, and/or yeast.

In general, for most preservatives, it is expected that the amount of preservative can be provided at a level of about 0.1 wt. % to about 1.0 wt. %, and can be provided at a level of about 0.2 wt. % to about 0.5 wt. %, based on the weight of the retinoid containing composition.

Antioxidants

The retinoid containing composition can include antioxidants to help increase the shelf life of the composition and to provide desired properties when applied to skin tissue. Exemplary antioxidants that can be used include vitamins such as vitamin E, vitamin E acetate, vitamin C, and vitamin D, and derivatives thereof. Exemplary antioxidants include α-tocopherols which can be characterized as natural or synthetic Vitamin E. Additional exemplary antioxidants include propyl, octyl and dodecyl esters of gallic acid, butylated hydroxyanisole (BHA)(usually as a mixture of ortho and meta isomers), butylated hydroxytoluene (BHT), and nordihydroguairetic acid, and alkylated parabens such as methylparaben and propylparaben.

The retinoid containing composition can be formulated without an antioxidant. When the retinoid containing composition includes an antioxidant, the antioxidant can be provided in an amount that provides antioxidant properties in the composition. In general, it is expect that the antioxidant can be provided in an amount of about 0.2 wt. % to about 2 wt. %, and can be provided in an amount of about 0.7 wt. % to about 1.5 wt. %, based on the weight of the composition. In the case of vitamin E, it is expected that the vitamin E can be included in the composition in an amount of about 0.1 wt. % to about 1 wt. %, and can be included in an amount of about 0.3 wt. % to about 0.8 wt. %.

Chelating Agents

Chelating agents are substances used to chelate or bind metallic ions with a certain heterocyclic ring structure so that the ion is held by chemical bonds from each of the participating rings. Suitable chelating agents include ethylene diaminetetraacetic acid (EDTA), EDTA trisodium, EDTA tetrasodium, calcium disodium edetate, EDTA trisodium, EDTA tetrasodium and EDTA dipotassium. One or more chelating agents can optionally be included in the emulsion in amounts ranging from about 0.001 to about 0.1 weight percent. It should be appreciated that the retinoid containing composition can be provided without a chelating agent.

Fragrances

Fragrances are aromatic compounds which can impart an aesthetically pleasing aroma to the retinoid containing composition. Typical fragrances include aromatic materials extracted from botanical sources (i.e. rose petals, gardenia blossoms, jasmine flowers, etc.) which can be used alone or in any combination to create essential oils. Alternatively, alcoholic extracts may be prepared for compounding fragrances. One or more fragrances can optionally be included in the composition in an amount ranging from about 0.001 to about 10 weight percent, preferably about 0.05 to about 5 percent. It should be appreciated that the retinoid containing composition can be provided without a fragrance.

Carriers, Diluents, and Excipients

The retinoid containing composition may also include non-toxic, pharmaceutically and dermatologically acceptable carriers, diluents and excipients, suitable for topical application, as are well known, see for example Merck Index, Merck & Co., Rahway, N.J., Bioreversible Carriers in Drug Design, Theory and Application, Roche (ed.) Pergamon Press, (1987), Gilman et al., (eds) (1990) Goodman and Gilman's: The Pharmacological Bases of Therapeutics, 8th Ed., Pergamon Press, Novel Drug Delivery Systems, 2nd Ed., Norris (ed.) Marcel Dekker Inc., (1989), and Remington's Pharmaceutical Sciences. For standard dosages of conventional pharmacological agents, see, e.g., Physicians Desk Reference (1997 Edition); and American Medical Association (1997) Drug Evaluations (Subscriptions).

Analgesics and Preservatives

The retinoid containing composition may also include analgesics and preservatives. An exemplary mild topical analgesic that can be used is available under the name allantoin. An exemplary preservative that can be included in the composition includes phenoxyethanol.

EXAMPLES

A retinoic acid containing composition was tested for stability under an accelerated stability test condition that included holding the composition at 40° C. for 120 days. The retinoid containing composition is identified in Table 1.

TABLE 1

Retinoic Acid Containing Composition

| Components | Gms/L | Wt. % | ml |
|---|---|---|---|
| Water | 891.0 | 89.10 | 623.70 |
| Carbopol U-10 | 5.0 | 0.50 | 3.50 |
| Stearic Acid | 20.0 | 2.00 | 14.00 |
| Retinoic Acid | 1.0 | 0.10 | 0.70 |
| Pluronic P 123 | 8.0 | 0.80 | 5.60 |
| Invisicare C-5 | 60.0 | 6.00 | 42.00 |
| Triethanolamine | 5.0 | 0.50 | 3.50 |
| Vitamin E | 3.0 | 0.30 | 2.10 |
| Allantoin | 2.0 | 0.20 | 1.40 |
| Phenoxyethanol | 5.0 | 0.50 | 3.50 |
| Total | 1000.0 | 100.00 | 700.00 |

TABLE 2

Accelerated Stability Testing

| Retinoic Acid Detected in Composition (wt. %) | Days Accelerated Testing at 40° C. |
|---|---|
| 0.110 | 0 |
| 0.098 | 62 |
| 0.093 | 105 |
| 0.091 | 124 |

Table 2 reports accelerated age testing results, and correlates to a room temperature shelf life of 2-3 years. The polymer component utilized in the composition was Invisicare C-5 polymer from Skinvisible Pharmaceuticals, Inc. and can be characterized as a polymer adduct containing about 40 wt. % water and about 60 wt. % polymer adduct prepared from carboxymethyl cellulose and a mixture of poly(vinylpyrrolidone/1-eicosene) and poly(vinylpyrrolidone/hexadecene).

In another study, samples were prepared as shown in Table 1 except Vitamin E and allantoin were omitted, and 0.2% retinol (ROH) was substituted for the retinoic acid. In an additional study, samples were prepared as shown in Table 1 except Vitamin E and allantoin were omitted, and 0.3% retinyl palmitate was substituted for the retinoic acid.

Controls were prepared according to Table 3:

TABLE 3

Retinoic Acid

| Components | Gms/L | Wt. % |
|---|---|---|
| Water | 5.0 | 0.50 |
| Petrolatum | 986.0 | 98.60 |
| Retinoic Acid | 1.0 | 0.10 |
| Pluronic P 123 | 8.0 | 0.80 |
| | 1000.0 | 100.00 |

Similar controls were made with Retinol (ROH) and Retinyl Palmitate (RP). Samples and controls were maintained at 40° C. for the times indicated. The results of this study are shown in Table 4.

TABLE 4

Results of Retinoic Acid, Retinol and Retinyl Palmitate Study

| C-5 | Initial % | 30 Days % | 74 Days % | 109 Days % | 144 Days % | Total Loss % |
|---|---|---|---|---|---|---|
| RA | 0.127% | 0.126% | 0.112% | 0.106% | 0.102% | 19.56% |
| ROH | 0.162% | 0.113% | 0.094% | 0.091% | 0.091% | 44.16% |
| RP | 0.257% | 0.184% | 0.161% | 0.130% | 0.129% | 49.77% |
| RA Control | 0.059% | 0.026% | 0.022% | 0.022% | 0.021% | 65.08% |
| ROH Control | 0.112% | 0.068% | 0.066% | 0.057% | 0.053% | 52.30% |
| RP Control | 0.095% | 0.087% | 0.079% | 0.071% | 0.070% | 26.47% |

The data in Table 4 clearly show a stabilizing effect of the Invisicare C-5 polymer on retinoic acid (RA). This stabilizing effect was absent in the controls and in the retinol and retinyl palmitate compositions containing the Invisicare C-5 polymer.

The above specification, examples and data provide a complete description of the manufacture and use of the composition of the invention. Since many embodiments of the invention can be made without departing from the spirit and scope of the invention, the invention resides in the claims hereinafter appended.

I claim:

1. A method for stabilizing retinoic acid, the method comprising:
mixing retinoic acid with a hydrophobic polymer/hydrophilic polymer adduct comprising a poly(vinylpyrrolidone-alkylene) polymer and cellulose to form a retinoic acid containing composition comprising about 0.01 wt. % to about 0.15 wt. % of the retinoic acid, wherein the step of mixing comprises mixing in the presence of an oxygen containing atmosphere, wherein the retinoic acid containing composition retains at least about 70% of its original activity after accelerated testing at 40° C. for 120 days with exposure to an oxygen atmosphere.

2. A method according to claim 1, wherein the poly(vinylpyrrolidone-alkylene) polymer comprises a polymer having an alkylene group containing about 10 carbon atoms to about 30 carbon atoms.

3. A method according to claim 1, wherein the composition comprises at least about 50 wt. % water.

4. A method according to claim 1, wherein the composition comprises about 0.5 wt. % to about 6 wt. % of a surfactant.

5. A method according to claim 1, wherein the composition comprises about 0.1 wt. % to about 2 wt. % of a thickener.

6. A method according to claim 1, wherein the composition comprises about 0.5 wt. % to about 5 wt. % of a moisturizer.

7. A method according to claim 1, wherein the cellulose has a weight average molecular of about 50,000 to about 15,000,000.

8. A method according to claim 1, wherein the cellulose comprises cellulose gum.

9. A method according to claim 1, wherein the cellulose comprises carboxymethyl cellulose.

10. A method according to claim 1, wherein the hydrophobic polymer/hydrophilic polymer adduct comprises about 2 wt. % to about 28 wt. % of the hydrophilic polymer and about 72 wt. % to about 98 wt. % of the hydrophobic polymer.

11. A method according to claim 1, wherein the retinoic acid containing composition comprises about 3 wt. % to about 20 wt. % of the hydrophobic/hydrophilic polymer adduct.

12. A method according to claim 1, wherein the retinoic acid containing composition comprises about 4 wt. % to about 15 wt. % of the hydrophobic/hydrophilic polymer adduct.

13. A retinoic acid containing composition comprising:
(a) at least about 0.0001 wt. % retinoic acid;
(b) at least about 3 wt. % of a hydrophobic polymer/hydrophilic polymer adduct comprising a poly(vinylpyrrolidone-alkylene) polymer and cellulose;
(c) at least about 50 wt. % water;
(d) wherein the retinoic acid containing composition retains at least about 70% of its original activity after accelerated testing at 40° C. for 120 days with exposure to an oxygen atmosphere, and
(e) wherein the composition is made by mixing the polyvinylpyrrolidone-alkylene) polymer, cellulose, and retinoic acid in the presence of an oxygen containing atmosphere.

14. A retinoic acid containing composition according to claim 13 wherein the poly(vinylpyrrolidone-alkylene) polymer comprises a polymer having an alkylene group containing about 10 carbon atoms to about 30 carbon atoms.

15. A retinoic acid containing composition according to claim 13, wherein the composition comprises about 0.5 wt. % to about 6 wt. % of a surfactant.

16. A retinoic acid containing composition according to claim 13, wherein the composition comprises about 0.1 wt. % to about 2 wt. % of a thickener.

17. A retinoic acid containing composition according to claim 13, wherein the composition comprises about 0.5 wt. % to about 5 wt. % of a moisturizer.

18. A retinoic acid containing composition according to claim 13, wherein the composition comprises about 0.01 wt. % to about 0.15 wt. % of retinoic acid.

19. A retinoic acid containing composition according to claim 13, wherein the cellulose has a weight average molecular of about 50,000 to about 15,000,000.

20. A retinoic acid containing composition according to claim 13, wherein the cellulose comprises cellulose gum.

21. A retinoic acid containing composition according to claim 13, wherein the cellulose comprises carboxymethyl cellulose.

22. A retinoic acid containing composition according to claim 13, wherein the hydrophobic polymer/hydrophilic polymer adduct comprises about 2 wt. % to about 28 wt. % of the hydrophilic polymer and about 72 wt. % to about 98 wt. % of the hydrophobic polymer.

23. A retinoic acid containing composition according to claim 13, wherein the retinoic acid containing composition comprises about 3 wt. % to about 20 wt. % of the hydrophobic/hydrophilic polymer adduct.

24. A retinoic acid containing composition according to claim 13, wherein the retinoic acid containing composition comprises about 4 wt. % to about 15 wt. % of the hydrophobic/hydrophilic polymer adduct.

* * * * *